United States Patent [19]

Schmitz-Treyer et al.

[11] Patent Number: 6,013,465
[45] Date of Patent: Jan. 11, 2000

[54] METHOD FOR DETECTION AND DETERMINATION OF ENZYMATIC REACTIONS IN URINE

[75] Inventors: Ursula Schmitz-Treyer, München; Walter Hofmann, Unterhaching; Walter Guder, München, all of Germany

[73] Assignee: Dade Behring Marburg GmbH, Marburg, Germany

[21] Appl. No.: 09/157,105

[22] Filed: Sep. 18, 1998

[30] Foreign Application Priority Data

Sep. 19, 1997 [DE] Germany .................... 197 41 447

[51] Int. Cl.[7] .................... C12Q 1/44; C12Q 1/28; C12Q 1/00; G01N 33/53
[52] U.S. Cl. .................... 435/19; 435/28; 435/4; 435/968; 435/283.1; 435/289.1; 422/50; 422/55; 422/68.1
[58] Field of Search .................... 435/19, 28, 4, 435/968, 283.1, 289.1; 422/50, 55, 68.1

[56] References Cited

U.S. PATENT DOCUMENTS

| 4,637,979 | 1/1987 | Skjold et al. | 435/19 |
| 5,135,875 | 8/1992 | Meucci et al. | 435/19 |
| 5,516,700 | 5/1996 | Smith et al. | 435/19 |

FOREIGN PATENT DOCUMENTS

| 0 094 554 A1 | 11/1983 | European Pat. Off. . |
| 0 597 410 A1 | 5/1984 | European Pat. Off. . |
| 0 230 229 A2 | 7/1987 | European Pat. Off. . |
| 0 279 614 A2 | 8/1988 | European Pat. Off. . |

*Primary Examiner*—Louise N. Leary
*Attorney, Agent, or Firm*—Finnegan, Henderson, Farabow, Garrett & Dunner, L.L.P.

[57] ABSTRACT

The present invention relates to a method for the detection and for the determination of enzymatic reactions in urine, wherein certain substances which improve the optical measurability of the enzymatic reaction are added to the reaction.

19 Claims, No Drawings

METHOD FOR DETECTION AND DETERMINATION OF ENZYMATIC REACTIONS IN URINE

The present invention relates to a method for detection and determination of enzymatic reactions in urine, wherein certain substances which improve the optical measurability of the enzymatic reaction are added to the reaction.

In the diagnosis of disorders of the kidneys and of the urogenital tract, the detection of particular enzymes, especially pseudoperoxidases and esterases, in body fluids, especially in urine, is of great importance. Originally, physical methods such as, for example, centrifugation and counting of leukocytes, were particularly important in urine diagnosis. These methods are no longer practicable nowadays—although satisfactory in terms of the result—because they require a high degree of manual activity. Even the so-called "test strips" which are very widely used in urine diagnosis require a certain degree of manipulation, so that automation of the measurement from taking the sample to evaluation is scarcely possible. Particularly important parts of urine diagnosis are, on the one hand, detection of granulocyte esterases as a basic investigation forming part of urinalysis, and detection of blood in urine by means of the determination of pseudoperoxidases.

Measurement of these parameters using test strips has been able to persist in practice inter alia because test strips considerably simplify the measurement because of the chromatographic properties of the support material. Corresponding methods and means therefore have already been described.

It was therefore an objective of the invention to develop a wet chemical method for the determination of particular enzymes in urine. It has emerged, surprisingly, that optical determination of enzymes even in colored urines can easily be carried out in automatic analyzers by use of particular reagent additives.

A method for detection and determination of enzymatic reactions in urine is described, in which a urine sample containing enzymes to be detected is mixed with a specific substrate in an automatic analyzer, the enzymatic reaction is followed and measured optically, and a substance improving the measurability is added to the reaction, this substance being selected from the group of lower alcohols: methanol, ethanol and propanol.

It is advantageous in this connection to employ the alcohol in a concentration of about 1 to 70% by volume—in the reaction mixture—preferably about 10 to 60% by volume, particularly preferably 40 to 60% by volume, very particularly preferably 45 to 55% by volume.

The enzyme to be detected is advantageously hemoglobin pseudoperoxidase or leukocyte esterase.

To detect the reaction of hemoglobin pseudoperoxidase it is advantageous to employ TMB and to add at least one substance from the following group to the reaction mixture: 6-methoxyquinoline and phenanthridine, adding 6-methoxyquinoline in a concentration of 0.1 to 0.5% by volume and phenanthridine in a concentration of 1 to 3 mg/ml.

In order to detect leukocyte esterase, the substrate employed is the 3-hydroxy-5-phenylpyrrole N-tosyl-L-alanine ester known per se and a diazonium salt and at least one substance from the following group are added to the reaction mixture: Brij®, cholic acid, ethylene glycol and EDTA.

The diazonium salt is advantageously diazonium chloride zincate and is added in a concentration of 0.02 to 0.1 mg/ml, Brij® in a concentration of 0.1 to 0.5% by volume, cholic acid in a concentration of 0.02 to 0.3% by volume, ethylene glycol in a concentration of 0.1 to 0.5% by volume and EDTA in a concentration of 0.1 to 0.5 mmol/l.

To avoid interference by ascorbic acid it is possible to add ascorbate oxidase.

It is advantageous to carry out a double determination with the substrate being added in only one of the determinations, and the difference between the determination without and the determination with substrate being regarded as the measurement.

Abbreviations used:

| | |
|---|---|
| EDTA | Ethylenediaminetetraacetic acid |
| PBS | Phosphate-buffered saline |
| TMB | Tetramethylbenzidine |

The following examples are intended to illustrate the invention.

EXAMPLE 1

Wet Chemical Measurement of Leukocyte Esterase in Urine

The determination took place in a Hitachi 911 analyzer (Boehringer Mannheim, Germany). The following reagents were employed:

R1: 0.25 mol/l PBS, pH 7.5
   0.5% Brij®
   1.0% ethylene glycol
   0.25% cholic acid
   1 mmol/l EDTA R2: 2.5 mg of 3-hydroxy-5-phenylpyrrole N-tosyl-L-alanine ester in 9.8 ml of ethanol (96%)+0.2 ml of decanol R3: 0.625 mg/ml diazonium chloride zincate in distilled water R4: 70 ml of ethanol (96%)+30 ml of distilled water.

The measurement takes place as endpoint determination at 546 nm. The reagent volumes are:

R1: 40 $\mu$l
R2: 20 $\mu$l
R3: 20 $\mu$l
R4: 160 $\mu$l
Sample: 40 $\mu$l of undiluted urine

EXAMPLE 2

Wet Chemical Measurement of Hemoglobin Pseudoperoxidase in Urine

The determination took place in a Hitachi 911 analyzer (Boehringer Mannheim, Germany). The measurement took place as endpoint determination at 660 nm. The following reagents were employed:

R1: 0.1 mg/ml ascorbate oxidase in 0.1 mol/l phosphate buffered isotonic NaCl solution (PBS)

R2: 1.0 mol/l citrate buffer pH 4.8

R3: 45 mg of TMB
   +4 ml of R2
   +6 ml of ethanol (96%)
   +0.4 ml of 6-methoxyquinoline
   +280 mg of phenanthridine
   +200 mg of dihydroperoxide (Luperox®)

R4: 70 ml of ethanol (96%)+30 ml of distilled water.

The reagent volumes were:

| | |
|---|---|
| R1 | 20 μl |
| R2 | 1 μl |
| R3 | 20 μl |
| R4 | 190 μl |

Sample: 50 μl of undiluted urine

We claim:

1. A method for detection and determination of an enzymatic reaction in urine comprising
   a) mixing a urine sample containing an enzyme to be detected with a substrate in an automatic analyzer,
   b) following the enzymatic reaction and measuring the reaction option; and
   c) adding a lower alcohol to improve the measurability of the reaction.

2. The method as claimed in claim 1, wherein the alcohol is in a concentration of about 1 to 70% by volume in the reaction mixture.

3. The method as claimed in claim 1, wherein the enzyme to be detected is hemoglobin pseudoperoxidase.

4. The method as claimed in claim 2, wherein the enzyme to be detected is hemoglobin pseudoperoxidase.

5. The method as claimed in claim 3 for the determination of blood in urine.

6. The method as claimed in claim 4 for the determination of blood in urine.

7. The method as claimed in claim 2, wherein the enzyme to be detected is leukocyte esterase.

8. The method as claimed in claim 2, wherein the enzyme to be detected is leukocyte esterase.

9. The method as claimed in claim 3, wherein the substrate is tetramethylbenzidine and at least one substance selected from the group consisting of 6-methoxyquinoline and phenanthridine is added to the reaction mixture.

10. The method as claimed in claim 4, wherein the substrate is tetramethylbenzidine and at least one substance selected from the group consisting of 6-methoxyquinoline and phenanthridine is added to the reaction mixture.

11. The method as claimed in claim 9, further comprising adding 6-methoxyquinoline in a concentration of 0.1 to 0.5% by volume and phenanthridine in a concentration of 1 to 3 mg/ml to the reaction mixture.

12. The method as claimed in claim 10, further comprising adding 6-methoxyquinoline in a concentration of 0.1 to 0.5% by volume and phenanthridine in a concentration of 1 to 3 mg/ml to the reaction mixture.

13. The method as claimed in claim 7, wherein the substrate is 3-hydroxy-5-phenylpyrrole N-tosyl-L-alanine ester, and a diazonium salt and at least one substance selected from the group consisting of Brij®, cholic acid, ethylene glycol and EDTA are added to the reaction mixture.

14. The method as claimed in claim 8, wherein the substrate is 3-hydroxy-5-phenylpyrrole N-tosyl-L-alanine ester, and a diazonium salt and at least one substance selected from the group consisting of Brij®, cholic acid, ethylene glycol and EDTA are added to the reaction mixture.

15. The method as claimed in claim 13, wherein the diazonium salt is diazonium chloride zincate and is added in a concentration of 0.1 to 0.5% by volume, wherein Brij® is in a concentration of 0.1 to 0.5% by volume, wherein cholic acid is in a concentration of 0.02 to 0.3% by volume, wherein ethylene glycol is in a concentration of 0.1 to 0.5% by volume, and wherein EDTA is in a concentration of 0.1 to 0.5 mmol/l.

16. The method as claimed in claim 14 wherein the diazonium salt is diazonium chloride zincate and is added in a concentration of 0.1 to 0.5% by volume, wherein Brij® is in a concentration of 0.1 to 0.5% by volume, wherein cholic acid is in a concentration of 0.02 to 0.3% by volume, wherein ethylene glycol is in a concentration of 0.1 to 0.5% by volume, and wherein EDTA is in a concentration of 0.1 to 0.5 mmol/l.

17. The method as claimed in 1, further comprising adding ascorbate oxidase to the reaction mixture to avoid interference by ascorbic acid.

18. The method as claimed in claim 1, further comprising a double determination, wherein substrate is added in only one of the determinations, and wherein the difference between the determination without substrate and the determination with substrate is the measurement.

19. The method as claimed in claim 1, wherein the lower alcohol is selected from the group consisting of methanol, ethanol and propanol.

* * * * *

UNITED STATES PATENT AND TRADEMARK OFFICE
CERTIFICATE OF CORRECTION

PATENT NO. : 6,013,465
DATED : January 11, 2000
INVENTOR(S) : Ursula Schmitz-Treyer et al.

It is certified that error appears in the above-identified patent and that said Letters Patent is hereby corrected as shown below:

Claim 1, Column 3, Line 15, "option" should read --optically--.

Signed and Sealed this

Twenty-fourth Day of April, 2001

Attest:

NICHOLAS P. GODICI

*Attesting Officer*   *Acting Director of the United States Patent and Trademark Office*